United States Patent [19]

Pailin

[11] Patent Number: 4,687,476
[45] Date of Patent: Aug. 18, 1987

[54] TOPICAL DRESSINGS

[76] Inventor: Eric Pailin, 43 Park Mount Drive, Macclesfield, Cheshire, England, SK11 8TM

[21] Appl. No.: 719,284
[22] PCT Filed: Jul. 11, 1984
[86] PCT No.: PCT/GB84/00250
 § 371 Date: Mar. 14, 1985
 § 102(e) Date: Mar. 14, 1985
[87] PCT Pub. No.: WO85/00287
 PCT Pub. Date: Jan. 31, 1985

[30] Foreign Application Priority Data

Jul. 14, 1983 [GB] United Kingdom ............... 8319096

[51] Int. Cl.⁴ ............................................. A61F 13/02
[52] U.S. Cl. .................................... 604/307; 128/156; 206/484
[58] Field of Search ............ 206/531, 532, 534.2, 206/484; 604/289, 290, 305–309; 128/153, 156

[56] References Cited

U.S. PATENT DOCUMENTS

Re. 20,899 10/1938 Scholl .............................. 206/482
1,476,682 12/1923 Beckmann ..................... 128/153
2,082,820  6/1937 Alby .
2,599,523  6/1952 Dorr ................................ 128/153
2,918,062 12/1959 Scholl ............................. 128/153
3,063,448 11/1962 Scholl ............................. 128/153
3,212,495 10/1965 Osborn et al. .................. 604/307
3,814,095  6/1974 Lubens ............................ 604/307
4,127,339 10/1978 Malacheski et al. ............ 604/289
4,376,483  3/1983 Sullivan .......................... 206/484

FOREIGN PATENT DOCUMENTS 0008545 3/1980 European Pat. Off. ......... 206/531
2082820 3/1970 France .

Primary Examiner—C. Fred Rosenbaum
Assistant Examiner—Jerome R. Smith, Jr.
Attorney, Agent, or Firm—Fisher, Christen & Sabol

[57] ABSTRACT

A method of manufacturing topical dressings is provided. This method utilizes a continuous multi-layer strip having a continuous layer of a first foil and on one side thereof a laminated material comprising a layer of skin adhesive protected with a release film. The laminated material is divided into separate portions, each portion containing a respective aperture which holds a topical substance. A second foil is then disposed over the substance containing aperture. This second foil is separable between portions to define individual dressings.

3 Claims, 11 Drawing Figures

TOPICAL DRESSINGS

FIELD OF THE INVENTION

This invention relates to dressings for use in the topical administration of substances, particularly therapeutic substances.

BACKGROUND ART

It is known to administer drugs transdermally i.e. by maintaining a drug in intimate contact with a patient's skin so that the active constituent slowly passes through the skin and is absorbed into the patient's body over a prolonged period of time.

The drug is usually held in position for the requisite period of time using an adhesive patch, the drug being incorporated as an integral part of the patch for example by admixture with the adhesive. However, the problem arises that such patches can be inconvenient or difficult to manufacture especially where mass-production of different patches containing different drugs is required.

DISCLOSURE OF THE INVENTION

An object of the present invention is to overcome or at least minimise this problem.

According to the invention therefore there is provided a method of manufacturing topical dressings utilising a continuous strip-shaped assembly having successive longitudinally spaced locations respectively for receiving and retaining thereat a topical substance, characterised in that said locations comprise apertures in a protected layer of skin adhesive provided on one side of said assembly and a continuous length of sealing foil is applied to the opposite side thereof, said assembly being separable between said apertures into individual dressing structures each comprising a respective said aperture bounded on one side by said adhesive and sealed at its opposite side by said foil.

With this method the use of continuous lengths of material can much facilitate the manufacturing process, especially on a mass-production basis. Moreover, this advantage can be achieved essentially irrespective of the nature of the topical substance in so far as incorporation of such substance can be effected independently of the fabrication of the dressing structures by insertion thereof into the said preformed receiving apertures in a particularly simple and convenient manner.

The method of the invention may be utilised in the production of dressings for transdermal drug application. It is however to be understood that the invention is not intended to be restricted to this field of application and may find use in the context of therapeutic substances, such as skin creams, not necessarily required to be absorbed through the patient's skin, or even cosmetics or fragrances or other non-therapeutic substances. Moreover, the invention may be utilised in the manufacture of dressings for animal as well as human use.

The adhesive may be applied to a layer of absorbent microporous material (e.g. polyamide fabric) having slow release properties, the said apertures being arranged to pass through this material as well as the adhesive.

The adhesive may be any suitable hypoallergenic adhesive as customarily used on the skin and this may be provided with a protective peel-off backing film such as a siliconised paper such paper having holes therein in alignment with the apertures. A laminated strip comprising continuous layers of said microporous material, said adhesive and said backing paper, may be appropriately die-cut to define said protected adhesive bounded apertures.

With regard to the said foil this may be formed from a polyester/metal foil composite or other material which is thin, flexible and generally of an impervious nature. Such foil may be heat-welded in position (e.g. to the said microporous material) for example by heat fusion of a polyethylene film on the foil material.

The assembly produced with the method of the invention may be separated into individual dressing structures, for example by transverse tearing or cutting between the said locations, and then enclosed between sheets, for example clear plastics sheets, after insertion of therapeutic or other topical substances into the said receiving locations, thereby to define storable sachets which are to be opened prior to use. To facilitate said separation into the dressing structures, the assembly may be provided with transverse perforation lines. The said sachet-forming sheets may be applied such as to define wholly separate sachets or, alternatively, so as to define strip- or sheet-interconnected sachets which may be separated by perforation lines. Such sachets may be sealed by heat-welding the sheets around the separated dressings.

Alternatively, the assembly may be retained as a multi-dressing strip structure and only separated after incorporation of topical substance at said locations. It is even possible to maintain the assembly as a multi-dressing structure until ready for use, appropriate provision being made for ready separation of individual dressings when required for use. In this case sealing may be effected as described above between two films although alternatively to seal the filled apertures and thereby define sachets it is possible to arrange a second foil strip over the said one side of the assembly (prior to any separation into individual dressing structures) and secure this to the first said foil. The protected skin adhesive may be cut away to expose parts of the first foil strip prior to application of the second foil strip. Preferably the second foil strip is applied directly over each aperture containing the topical substance without any intermediate layer therebetween. Perforations in circle or box formation may be provided in the first foil strip around the said locations to permit removal of the dressings.

As indicated above, the said substance may be of any suitable kind preferably although not necessarily therapeutic and correspondingly such substance may be of any suitable physical form and carried in any suitable medium (e.g. solid, wax, cream, oil, gel etc) and may be introduced into the said locations in any suitable manner. Most preferably, each location will contain a carefully dosed quantity of the pertaining substance. Preferably also the topical substance is inserted into each aperture in a form in which it is capable of adhering to the first said foil.

BRIEF DESCRIPTION OF THE DRAWINGS

The invention will now be described further by way of example only and with reference to the accompanying drawings in which.

BEST MODE OF CARRYING OUT THE INVENTION

Figure 1:
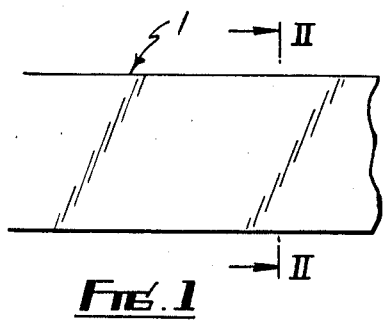
FIGS. 1, 3, 5 and 7 are plan views of strip-shaped structures used at different stages in the production of an assembly of interconnected dressing structures in accordance with one embodiment of the invention.
Figure 2:
FIGS. 2, 4, 6 and 8 are sectional views respectively on lines II—II, IV—IV, VI—VI and VIII—VIII of FIGS. 1, 3, 5, and 7.
Figure 3:
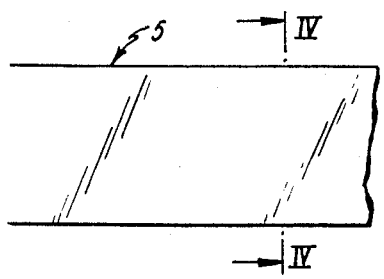
Figure 4:
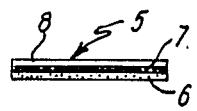

With reference to the drawings, an assembly of interconnected dressing structures is formed from a continuous length of flexible foil 1 (as shown in FIGS. 1 and 2), comprising metal foil 3 laminated on opposite faces to a reinforcing polyester film 2 and a heat sealing polyethylene film 4, and a continuous flexible strip 5 (as shown in FIGS. 3 and 4) comprising a main body layer 6 of microporous material having on one face a layer of hypoallergenic skin adhesive 7 covered with an easy release protective backing paper 8. The layers 2 to 4 and 6 to 8 are all of the same width.

Figure 5:
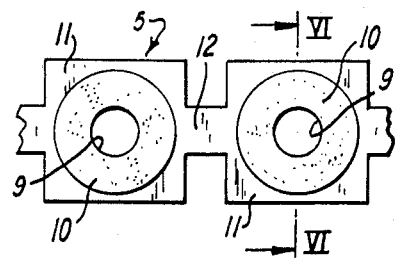
Figure 6:
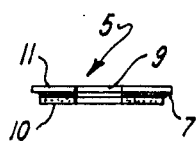

The strip 5 is fed continuously from a reel through a die-cutting machine which cuts circular holes 9 (as shown in FIGS. 5 and 6) completely through the strip 5 at equally spaced positions, the centres of such holes 9 lying on the longitudinal middle axis of the strip 5. At the same time the microporous material 6 is cut to define rings 10 around the holes 9, and the backing paper 8 is cut to define square sections 11 slightly smaller in width than the uncut paper 8 and joined by narrow linking sections 12 disposed symmetrically about the longitudinal axis of the strip 5. The removed microporous material 6 with attached adhesive layer 7 and backing paper 8 is discarded.

The die-cut strip 5 and the foil 1 are fed to a blocking head at which the foil 1 is superimposed on the strip 5 so that the polyethylene film 4 of the foil 1 is in contact with the microporous material 6. Circular heat seal lines 13, 14 are defined between the foil 1 and the strip 5 respectively slightly outwardly of the hole peripheries and slightly inwardly of the outer ring peripheries (i.e. by application of heat which causes the polyethylene film 4 to fuse and stick to the microporous layer 6). Circular perforation lines 15 are formed through the strip 1 completely around the outer heat seal line 14 except for a small gap where there is provided a cut lift-up tab 16. Circular dressing structures are thereby defined within the perforation lines 15 (and tabs 16). Alignment of the strip 1 at the blocking head is effected with the aid of a light beam and sensor which detects the leading edges of the holes 9.

The resulting strip-shaped assembly is wound onto a reel and can be stored and transported in this condition as required.

Figure 9:
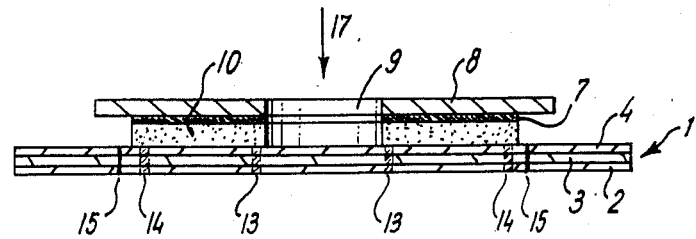
FIG. 9 is a sectional view to a larger scale of the arrangement of FIG. 8 during filling with a therapeutic substance.
Figure 10:
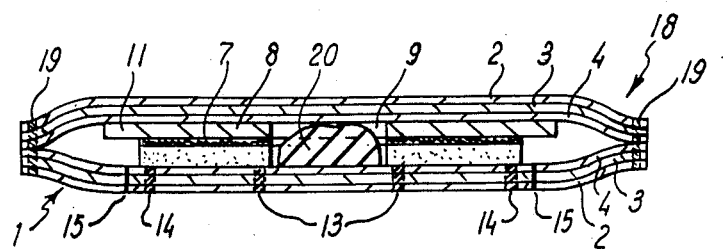
FIG. 10 is a sectional view showing the arrangement of FIG. 9 after filling and after sealing to form a finished dressing.

As shown in FIG. 9 the holes 9 are open at one end (via the paper 8) and are sealed at the other end (by the foil 1) thereby defining receptacles. These receptacles can be filled with a therapeutic substance as follows:

The reel is mounted on a spindle and is fed to a dispense head. At such head a closed quantity of substance is inserted into the receptacle (in the direction of arrow 17). The substance is generally of a self-supporting consistency and this may comprise an absorbent pad impregnated with the substance or a mass of the substance for example in gel form. The substance should be capable of being retained within the receptacle and thus may be in the form of a tacky material which adheres to the foil 1 and then quickly dries or sets. Alternatively or additionally, where a pad is used this may be the same size and shape as the receptacle so as to be wedged therein. After allowing time for setting (if necessary) the filled structure is then sealed by application of a second strip 18 of the same material (and dimensions) as the strip 1. The two strips 1, 18 are exactly superimposed and heat sealed together (at 19) around the entire peripheries of the square sections 11 of the backing paper 8. In this respect it will be appreciated that the two foils 1, 18 project beyond the backing paper 8 and can therefore be brought into contact with each other to achieve a strong bond.

Figure 7:
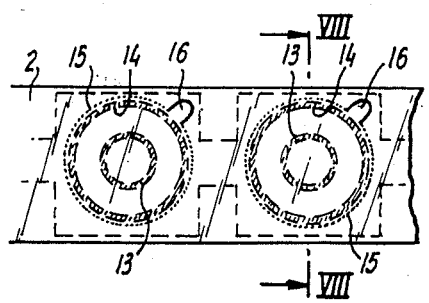
Figure 8:
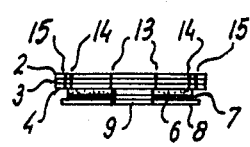

The substance 20 is thereby held securely in the sealed receptacle between the foils 1, 18. Individual sealed receptacles may be detached as a final manufacturing stage by transverse slitting through the centres of the linking sections 12. Alternatively the sealed receptacles may be retained interconnected in rolls or strips of any suitable number. Other arrangements are also possible. Thus, if desired, the structure shown in FIGS. 7 and 8 may be transversely cut to give individual receptacles before filling and sealing.

Figure 11:
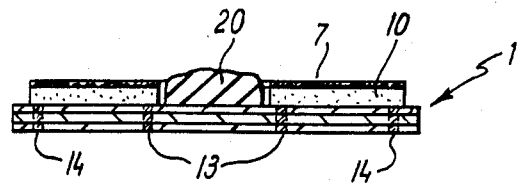
FIG. 11 is a sectional view of the finished dressing opened and ready for application to the skin.

In use, a sachet or sealed receptacle is opened by lifting the tab 16 and breaking the bottom foil 1 at the perforations 15. The resulting circular piece of foil 1 is removed together with the attached ring 10 and therapeutic substance, as shown in FIG. 11, it being understood that the adhesive 7 peels readily off the backing paper 8 and leaves this held sandwiched against the top foil 18 by the remaining part of the foil 1. It will also be understood that the substance 20 adheres to the foil 1 more strongly than to the foil 18.

The resulting dressing is then bonded to the skin with the adhesive 7 to hold the incorporated therapeutic substance in intimate contact therewith. The structure of the dressing and the impervious nature of the foil 1 holds the therapeutic substance securely captive on the skin although some "breathing" is possible through the microporous material via the side edges of the dressing.

With the above-described embodiment the dressing structures can be readily filled and securely closed, and advantageous manufacture can be achieved on a mass production basis whilst ensuring adequate levels of hygiene and security. Moreover, the resulting dressings are particularly convenient to use, and effective medication can be achieved whilst avoiding escape of substances likely to contaminate clothing.

It is of course to be understood that the invention is not intended to be restricted to the details of the above embodiments which are described by way of example only.

Thus, for example, the assembled strip structures may be fan-folded rather than reeled if this is more convenient (e.g. if the structure is bulky).

The dressings need not be circular as shown but may be square or oval or any other suitable shape as required.

The tab 16 can be omitted whereby the perforations 15 extend around the complete periphery and the dressings are removed by application of finger pressure through the top foil 18.

As described the receptacles are sealed by the foil 18 with no intermediate layer and the substance 20 is completely exposed after removal of the dressing. This arrangement can facilitate both manufacture and use; however, it is also possible to incorporate a gauze strip or the like over the filled receptacle as required. Such strip may be incorporated between the paper 8 and the foil 18. This may be helpful in retaining the substance in position in the receptacles where the substance 20 is a cream.

Instead of sealing the receptacles by heat welding the foil 1 to a second foil 18, it is possible to enclose the strip-shaped assembly of filled receptacles between two heat-welded films (additional to the strips 1 and 5), e.g. films of the above-described foil or simply polyethylene. The resulting assembly may be cut transversely to give individual sachets or may be left as a strip of interconnected sachets. In the latter case transverse perforations may be provided to facilitate separation. With this arrangement it will be appreciated that the backing paper 8 (and possibly also the material 6) need not be cut (except for the central hole 9).

It is also possible to use foil strips 1 and 18 which are of a common width greater than that of the strip 5 whereby heat sealing can be effected therebetween at the overlapping edges. In this case the backing paper 8 (and possible the material 6) need not be cut (except for the central hole 9).

In some circumstances it may be possible to omit the inner heat seal 13, relying instead solely on the outer heat seal 14.

It may also be possible to extend the material 6 beyond the perforations 15 (e.g. so that the material 6 is coextensive with the backing paper 8) and in this case the perforations may pass through the material 6 as well as the foil 1.

Where the substance 20 is bulky it may be helpful to emboss the foil 1 in the vicinity of the hole 9 to increase the capacity of the receptacle.

I claim:

1. A method of manufacturing topical dressings utilizing a continuous multi-layer strip having a continuous layer of a first foil and on one side thereof a laminated material comprising a layer of skin adhesive protected with a release film, said laminated material being shaped to define at successive locations spaced along the strip separate portions of said laminated material bounded by regions of said first foil, wherein said regions are free of skin adhesive, said portions each having a respective aperture therein, wherein a topical substance is introduced into each said aperture, and a continuous strip of a second foil is disposed over said laminated material and secured to said first foil around said portions so as to seal said apertures and thereby retain said topical substance within same, said multi-layer strip with said attached second foil being separable between said portions to define individual dressings each containing said topical substance in a respective said aperture bounded by said material and sealed between said first and second foils, and said second foil being separable from said portion in such individual dressing structure so that said skin adhesive and the topical substance can be exposed for use.

2. A method according to claim 1, including the step of forming said multi-layer strip from a continuous length of said laminated material, part of said material being cut away to define said portions prior to attachment of the second foil to the multi-layer strip.

3. A method of manufacturing topical dressings utilizing a continuous multi-layer strip having a continuous layer of a first foil and on one side thereof a laminated material comprising a layer of skin adhesive protected with a release film, said laminated material being cut away to define at successive locations spaced along the strip separate portions of said laminated material bounded by regions of said first foil, wherein said regions are free of skin adhesive, said portions each having a respective aperture therein, wherein a topical substance is introduced into each said aperture, and a continuous strip of a second foil is disposed over said laminated material and secured to said first foil around said portions so as to seal said apertures and thereby retain said topical substance within same, said multi-layer strip with said attached second foil being separable between said portions to define individual dressings each containing said topical substance in a respective said aperture bounded by said material and sealed between said first and second foils, and said second foil being separable from said portion in such individual dressing structure so that said skin adhesive and the topical substance can be exposed for use.

* * * * *